United States Patent [19]

Rosenstein

[11] Patent Number: 4,582,810
[45] Date of Patent: Apr. 15, 1986

[54] IMMUNO-AGGLUTINATION PARTICLE SUSPENSIONS

[75] Inventor: Robert Rosenstein, Ellicott City, Md.

[73] Assignee: Becton, Dickinson and Company, Paramus, N.J.

[21] Appl. No.: 537,737

[22] Filed: Sep. 30, 1983

[51] Int. Cl.$^4$ ................ G01N 33/544; G01N 33/545; G01N 33/549; G01N 33/53

[52] U.S. Cl. .................................. 436/528; 436/531; 436/532; 436/533; 436/534; 436/548; 436/823; 435/181

[58] Field of Search ................ 436/501, 528, 531–534, 436/823, 548; 435/181

[56] References Cited

U.S. PATENT DOCUMENTS

| | | | |
|---|---|---|---|
| 4,220,565 | 9/1980 | Katz | 260/6 |
| 4,228,237 | 10/1980 | Hevey et al. | 435/7 |
| 4,276,206 | 6/1981 | Katz | 260/6 |
| 4,282,287 | 8/1981 | Giese | 428/407 |
| 4,298,685 | 11/1981 | Parikh et al. | 435/7 |
| 4,352,884 | 10/1982 | Nakashima et al. | 435/531 |
| 4,419,444 | 12/1983 | Quash | 436/531 |

OTHER PUBLICATIONS

Rappuoli et al., "Competitive Enzyme Immunoassay for Human Chorionic Somatomammotropin Using the Avidin–Biotin System", *Analytical Biochemistry*, 118, 168–172, (1981).

Guesdon et al., "The Use of Avidin–Biotin Interaction in Immunoenzymatic Techniques", *The Journal of Histochemistry and Cytochemistry*, vol. 27, No. 8, pp. 1131–1139, 1979.

Berman et al., Amplification of the Biotin–Avidin Immunofluorescence Technique", Journal of Immunological Methods, 36 (1980), pp. 335–338.

*Primary Examiner*—Christine M. Nucker
*Attorney, Agent, or Firm*—Fitch, Even, Tabin & Flannery

[57] ABSTRACT

A suspension of diagnostic particles comprising antibody molecules attached to a carboxylate derivatized polymer core is provided for agglutination tests. The antibody is linked to the core through an avidin-biotin bridge. Avidin is joined by an amide bond to carboxyl groups on the core, and biotin is linked by an amide bond to amino groups on the antibody molecule. The core-bound antibody is exposed to a mixture of free biotin and biotinylated antibody to attach a controlled amount of antibody that is consistent with suspension stability prior to its use in a test and rapid cross-linking of suspended particles in the presence of antigen.

28 Claims, No Drawings

IMMUNO-AGGLUTINATION PARTICLE SUSPENSIONS

The present invention relates to tests which employ antibodies to detect the presence of particular antigenic substances and more particularly to improved suspensions of antibody molecules bound to solid support particles which agglutinate in the presence of the particular antigen to which the antibody is reactive.

BACKGROUND OF THE INVENTION

Antibodies are large proteinaceous molecules that are produced by animals in response to the presence of a foreign substance for the purpose of neutralizing that substance. An antibody molecule may be highly specific, recognizing only a certain site of a particular molecule which is the antigen to that antibody. Because of their high specificities, antibodies are very useful in ascertaining the presence or absence of various antigenic substances, and a number of test procedures, such as radioimmunoassays, have been developed to take advantage of the specificity of the antibodies. Relatively recently, monoclonal antibodies have been developed, providing a practical method for assuring that an antibody fraction contains only a single type of antibody molecule. Monoclonal antibodies may be substituted for conventional antibody fractions in most diagnostic tests, providing greater accuracy and reliability than tests which utilize conventional antibody fractions.

One particular type of test which has been developed that is particularly useful for detecting the presence of large antigens having multiple antibody-recognition sites (antigenic determinants), is an agglutination test. Antibody molecules are bound to minute particles formed of a polymer, and the particle-bound antibody is suspended in a liquid medium. In the presence of the antigen, the particle-bound antibody attaches to the recognition sites on the antigen. If antibody molecules on more than one particle attach to the same antigen molecule, the particles become cross-linked, and as multiple particles cross-link, they agglutinate and precipitate from the solution. Agglutination and precipitation of the suspended particles is readily observable by the naked eye, providing a very simple and very certain test that a particular antigen is present.

One currently used method of attaching antibodies to polymer particles is described in Molday, R. S., W. J. Dreyer, A. Rembaum, and S. P. S. Yen; "New Immunolatex Spheres: Visual Makers of Antigens on Lymphocytes for Scanning Electron Microscopy", *J. Cell Biol* (1975) 64, pp. 75–88. Carboxylate derivatized latex particles are reacted with the antibody in the presence of a carbodiimide, coupling amino groups on the antibody to the carboxyl groups on the peptide. This procedure is useful for binding relatively small antibody or immunoglobulin molecules, such as IgG, but does not work in acceptable fashion for binding larger antibody molecules such as IgM. Furthermore, this method provides no method for controlling the amount of antibody that binds to the particle. If excessive amounts of antibody bind to the particles, the particles may tend to agglutinate prematurely, i.e., before indroduction of the antigen.

Another method of binding antibodies to latex particles is through adsorption of antibodies to the surface of latex particles, as is described in Carel J. Van Oss and J. M. Singer; "The Binding of Immune Globulins and Other Proteins by Polystyrene Latex Particles", *J. Reticuloendothelial Soc.* (1966) 3, pp. 29–40. The success of this procedure depends to a great extent on the exact lot of the latex, different lots having vastly different adsorptive properties and stabilities. Because of the unpredictability of results, this procedure is used largely for larger antibody molecules, such as IgM.

It would be desirable to provide latex particles having bound antibody which can be more reproducibly manufactured, irrespective of the type of antibody and irrespective of the adsorptive properties of the particular lot of latex particles. It would be further desirable to control the number of antibody molecules binding to the particles to assure that premature agglutination will not occur due to the particles having excessive bound antibody molecules and yet assure that there are sufficient bound antibody molecules to agglutinate the particles rapidly in the presence of the antigen.

SUMMARY OF THE INVENTION

The invention provides a diagnostic composition comprising a suspension of carboxylate-derivatized latex particles bound to antibody molecules through avidin-biotin bridges. The latex particles, having multiple free carboxyl groups on their surfaces, are bound to avidin using a carbodiimide intermediate. Biotin is covalently bound to the antibody. A mixture of biotin and biotinylated antibody in a predetermined molar ratio are reacted with the latex-bound avidin, linking antibody moieties to a selected portion of the avidin binding sites. The number of antibody molecules attached through avidin-biotin bridges to the latex is controlled to assure that the particles remain in suspension until they cross-link and agglutinate in the presence of an antigen to the antibody.

DETAILED DESCRIPTION OF THE PREFERRED EMBODIMENTS

In accordance with the invention, diagnostic particles are provided in which antibodies are attached to carboxylate-derivatized latex particles through avidin-biotin bridges. The diagnostic particles comprise carboxylate-derivitized polymeric core particles, avidin moieties linked through amide bonds to the core particles, biotin moieties complexed to the avidin moities and antibody (immunoglobulin) molecules linked to the biotin moieties through amide bonds. The diagnostic particles are suspended in a liquid medium to form a latex composition that is useful for diagnosing the presence of an antigen to which the bound antibody is specific. The diagnostic particles suspended in the liquid medium agglutinate by cross-linking through antigen molecules that have multiple antigenic determinants that are recognized by the antibody, and the cross-linked diagnostic particles precipitate from the liquid medium.

To form the diagnostic particles, carboxylate-derivatized latex core particles are attached to avidin through an amide bond formed between the surface carboxyl groups of the polymeric core particle and primary amino groups on the avidin. An antibody of interest is attached to biotin through an amide bond formed by the carboxyl group of biotinic acid and an amine group of the antibody. Avidin has a very strong affinity for biotin, and the antibody-bound biotin moiety readily complexes to an avidin moiety linked to the core particle. To assure that the diagnostic particles will be stable as a latex suspension until agglutination testing, the number of antibody moieties linked to each core particle is controlled. To prevent excessive biotinylated antibody from complexing to the avidin moieties linked to the core particles, a mixture of free biotinic acid and biotinylated antibody of a predetermined molar ratio is reacted with the core particle-bound avidin so that biotinic acid occupies a portion of the binding sites on the avidin which might otherwise be occupied by the biotinylated antibody.

The term "latex" herein is used broadly to include stable dispersions of particles of polymeric material. Suitable latexes include suspensions of minute polystyrene and polyacrylamide particles. To provide that a stable suspension of the diagnostic particle can be formed which will precipitate within a reasonable time upon exposure to the antigen, the starting polymeric core particles should be between about 0.2 and about 1.0 micron in diameter.

The polymeric core particles are carboxylate-derivatized to provide exposed carboxyl groups at their surfaces for attachment of avidin. Polyacrylamide particles may be derivatized by the method of John K. Inman, "Covalent Linkage of Functional Groups, Ligands, and Proteins to Polyacrylamide Beads", in *Methods in Enzymology*, Vol XXXIV, (ed. William B. Jakoby and Meir Wilchek, Academic Press, N.Y., 1974) pp. 30–58. Suitable carboxylate-derivatized latex particles are commercially available; for example, carboxylate-latex sold by Polysciences. It is found that particles carboxylated to between 0.1 and about 0.5 milliequivalents per gram are most suitable. This degree of carboxylation provides more surface carboxyl groups than are eventually used to bind avidin and, subsequently, biotinylated antibody. However, less successful results are achieved with particles carboxylated to a lesser degree. Therefore, it is not considered desirable to limit the amount of antibody bound on each particle through the number of carboxyl moieties on the polymeric core particles.

The high affinity of avidin for biotinic acid is well known, and the combination of avidin and biotin are found to provide a very effective means for linking controlled amounts of antibody to the latex. Biotin (hexahydro-2-oxo-1H-thieno [3,4] imidazole-4-pentanoic acid) is a growth factor present in very minute amounts of every living cell and is found mainly bound to proteins or polypeptides. Avidin is a glycoprotein containing four essentially identical peptide subunits, each having an attached carbohydrate moiety. Each subunit of avidin has a single biotin binding site. The combined molecular weight of the subunits is about 66,000. Avidin is most commonly isolated from raw egg whites but is probably found in the genital tract of all animals. Avidin is also produced by certain bacteria, such as Streptomyces avidinii, and avidin used herein is to be understood to refer to animal avidin as well as bacterial avidin, such as streptavidin. The high affinity of avidin for biotin has been demonstrated by the ability of large amounts of avidin to produce biotin deficiency in rats and chicks.

Because the core particles have a greater number of surface carboxyl groups than are to be eventually linked to antibody molecules, avidin is reacted with the core particles in amounts less than the stoichiometric concentration which would link to all core surface carboxyl groups. It is not preferred, however, to control the number of biotinylated antibody molecules that are subsequently linked to the cores by limiting the number of avidin molecules that are bound to the cores to the minimum that would be required to complex stoichiometrically to the desired number of biotinylated antibody molecules. It is found that best results are achieved when avidin is reacted with the latex particles to provide between about $10^{10}$ and about $10^{13}$ molecules of avidin per $cm^2$ of estimated core particle surface area, and to this end, between about $1.2 \times 10^{-3}$ and about $1.2 \times 10^{-2}$ gm of avidin are reacted per gm of styrene core particles, and between about $1.2 \times 10^{-3}$ and about $1.2 \times 10^{-2}$ gm of avidin are reacted per gm of polyacrylamide core particles.

The antibody is selected according to the antigen to be detected. Any of the known types of immunoglobulins can be linked to latex core particles by the method of the present invention, including IgG, IgA and IgM. A general requirement is that the antibody be specific for an antigen having at least two antigenic determinants so that the antigen can bind to antibodies on different diagnostic particles and thereby cross-link the particles. Many large antigens of interest, such as the group carbohydrate antigen of Group A Streptococcus, have multiple, substantially identical, antigenic determinants. If the particular antigen does not have duplicate antigenic determinants, it may have spaced-apart distinct antigenic determinants, in which case a mixture of two or more antibodies, each reactive with one of the determinants, might be linked to the latex core particles to allow cross-linking between diagnostic particles to take place through the unique antigenic determinants.

It is preferred that, if available, monoclonal antibodies be used to detect antigens. Monoclonal antibodies, consisting of identical antibody molecules, are much more specific than conventionally obtained antibody fractions and provide for much greater reproducability between lots of diagnostic particles. "Monoclonal antibodies" is used herein to refer to antibodies generated by hybridomas, as well as antibodies produced by other cell immortalization techniques, e.g., by infection with certain viruses. However, the invention is intended to encompass diagnostic particles incorporating conventional antibody fractions, particularly to detect antigens for which no monoclonal antibody is presently available.

The formation of the amide bond between the carboxyl groups on the latex core particles and an amine group of the avidin is preferably facilitated through an intermediate formed by reaction of a crabodiimide, such as 1-ethyl-3-(3-dimethylaminopropyl) carbodiimide, with the carboxyl groups on the latex particles. After the carboxyl groups have been activated through reaction with the carbodiimide, the avidin is introduced, whereupon primary amino groups on the avidin replace the carbodiimide linked to the carbonyl. These reactions are represented in equation 1 below:

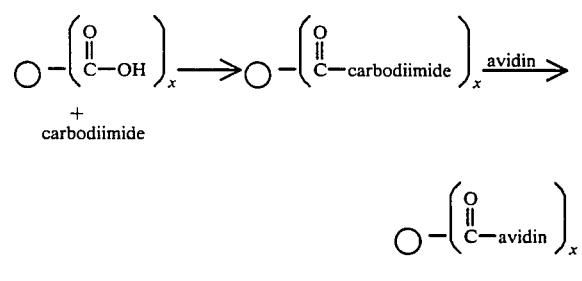

A preferred method of forming the amide bond between the carboxyl group of biotin and an amino group of the antibody molecule is by initially forming an ester between an N-hydroxy imide, such as N-hydroxy-succinimide and biotin and then reacting the N-hydroxy imide-biotin with the immunoglobulin, whereupon an amino group of the immunoglobulin replaces the N-hydroxyimide linked to the carbonyl. This reaction is carried out at slightly alkaline conditions, preferably at a pH of between about 7.5 and about 9.0. These reactions are represented in equation 2 below:

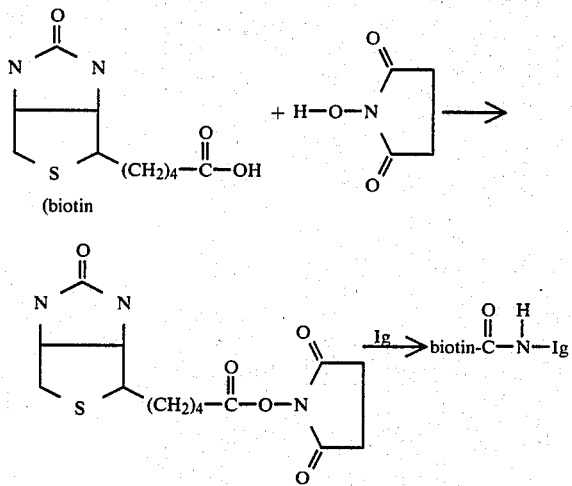

Because avidin is reacted in less than stoichiometric amounts, unbound surface carboxyl groups remain on the latex core particles. These unbound carboxyl groups are preferably neutralized, e.g., with an amine, such as ethanol amine.

It has been found that diagnostic particles have greater stability if, subsequent to neutralization, non-immunogenic proteinaceous material, such as bovine serum albumin (BSA), is adsorbed onto the surfaces of the avidin-bound latex core particle.

Control of the amount of antibody on the surface of the diagnostic particle, which is accomplished by mixing free biotinic acid with biotinylated antibody so that they compete for the excess avidin binding sites, is considered an important aspect of the invention. Too few antibody molecules may not afford agglutination at a suitable rate, whereas too many antibody molecules may result in premature precipitation. Generally, it is preferred that between $2 \times 10^{11}$ and about $2 \times 10^{12}$ antibody molecules be bound per cm$^2$ of estimated surface area of the latex core particles, although this may vary somewhat depending upon whether the antibody is small, e.g., IgG, or large, e.g., IgM. The molar ratio of biotinic acid to biotinylated antibody ratio is dependent on the number of avidin binding sites. It must also be taken into account that free biotinic acid reacts somewhat more rapidly with the avidin than does the antibody-bound avidin. Providing a desired amount of antibody on the diagnostic particles generally requires that a mixture of biotinic acid and biotinylated antibody in a molar ratio of between about 1:1 and about 10:1 be reacted with particles having avidin, in the above-mentioned preferred amounts, bound to the core particles. The reaction between a mixture of biotinylated antibody and biotinic acid with core particle-linked avidin is represented in equation 3 below:

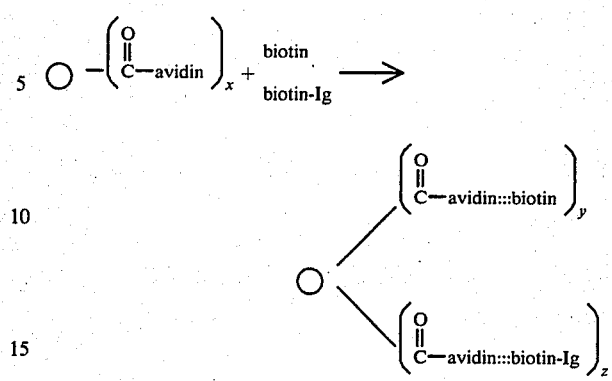

The liquid medium in which the diagnostic particles are suspended is generally aqueous as is consistent with the natural environment of antibody molecules. A slightly basic pH, e.g., between about 7.5 and about 8.5, contributes to stability of the diagnostic particles. Antimicrobial agents, such as NaN$_3$ may also be added to the medium. Generally latex suspensions for use in agglutination tests contain between about 5 and about 10 gm. of particles per liter of suspension.

The invention will now be described in greater detail by way of example.

EXAMPLE 4.0 ml of carboxylate-latex at 2.5 weight percent solids, obtained from Polysciences Inc. Warrington, Pa., is washed three times with distilled water, and after the final wash, the particles are resuspended in 4.0 ml of distilled water. 1.0 ml of 0.05 M KH$_2$PO$_4$, pH 4.5 is added. The suspension is placed on a magnetic stirrer and maintained at 22° C., and 5 ml. of a solution of 2 weight percent 1-ethyl-3-(3-dimethylaminopropyl) carbodiimide (obtained from Sigma Chem. Co., St. Louis, Mo.) is added and allowed to react with the latex for 3.5 hours. The carbodiimide-activated carboxylate-latex is then washed once in saline and resuspended in 5 ml of saline.

1.2 mg of avidin (all procedures are performed in duplicate, once using egg white avidin and once using streptavidin) is dissolved in 5 ml of 0.2 M borate, pH 8.5, and the 5 ml. latex suspension is added. The carbodiimide-activated carboxylate-latex and avidin are allowed to react for 20 hrs. at 22° C. To neutralize surface carboxyl groups that are not bound to avidin, 5 mM ethanolamine is added, and then BSA is added to a concentration of 2 weight percent. The avidin-latex is washed and taken up in 0.1 M glycine-saline, pH 8.2 containing 0.2% NaN$_3$, 0.2% BSA and 0.05% Tween-20 and stored at 4° C.

Antibodies are bound to biotin as follows:

(A) 1 mg of polyvalent rabbit IgG (anti-group A streptococcal antigen) in 1.0 ml. of 0.2 M NaHCO$_3$ is reacted with 50 μl of a solution of d-biotin-N-hydroxysuccinimide ester in DMSO (1.0 mg/ml). The reaction is allowed to proceed for 4 hours at 22° C., and the reaction mixture is then dialyzed at 4° C. for 18 hours against a 500-fold excess of 0.91 M tris-saline buffer, pH 8.0 containing 0.2% NaN$_3$.

(B) 1.0 mg of mouse monoclonal IgG$_3$ (anti-group A streptococcal antigen) in 1.0 ml of 0.2 M NaHCO$_3$ is reacted with 8 μl of a solution of d-biotin-N-hydroxysuccinimide ester in DMSO (1.0 mg/ml). The reaction is allowed to proceed for 4 hours at 22° C., and the reaction mixture is then dialyzed at 4° C. for 18 hours against a 500-fold excess of 0.01 M tris-saline buffer, pH 8.0 containing 0.2% NaN$_3$.

(C) 1.0 mg of mouse monoclonal IgM (anti-N meningitis B capsular polysaccharide) in 1.0 ml of 0.2 M NaHCO$_3$ is reacted with 8 to 10 μl of a solution of d-biotin-N-hydroxysuccinimide ester in DMSO (1.0 mg/ml) for 4 hours at 22° C., and the reaction mixture is then dialyzed against a 500-fold excess of 0.01 M tris-saline buffer, pH 8.0 containing 0.2% NaN$_3$.

Each of the biotinylated antibodies, formed above, is attached to the avidin-latex particles. 1.0 ml. of avidin latex is pelleted and the supernatant removed. The pellet is taken up in 1.0 ml of biotinylated antibody containing 5 μl of $10^{-3}$M biotinic acid, and the mixture is stirred for 1 hour at 22° C. to react the biotin and biotinylated antibody. After 1 hour, a second 5 μl aliquot of $10^{-3}$M biotinic acid is added to block potentially unoccupied biotin binding sites on the avidin moieties.

The diagnostic particles are centrifuged, washed and suspended at 0.6% solids in 0.1 M glycine-saline buffer, pH 8.2 containing 0.2% NaN$_3$, 0.2% BSA and 0.05% Tween-20.

To 15 ml of the diagnostic particle suspension formed from the polyvalent rabbit IgG, 50 ml containing 0.1 μg of Group A Streptoccous antigen are added. Agglutination of the suspension is noted after 4 minutes.

To 15 ml of the diagnostic particle suspension formed from the mouse monoclonal IgG$_3$ antibody, 50 ml containing 0.1 μg of Group A Streptococcus antigen are added. Agglutination of the suspension is noted after 10 minutes.

To 15 ml of the diagnostic particle suspension formed from the mouse monoclonal IgM antibody, 50 ml containing 0.1 μg of N mening B polysaccharide antigen are added. Agglutination of the suspension is noted after 10 minutes.

Suspensions of diagnostic, particles prepared according to the present invention, are stable if stored under refrigeration for periods of several months. The diagnostic particles are extremely sensitive, and using microtechniques, the suspensions can be used to detect as little as nanogram quantities of antigen.

Several advantages of the present invention can now be more fully appreciated. The invention provides for attachment of all types of immunoglobulins, including IgM. The amount of antibody attached to the latex is not dependent upon the adsorption characteristics of a particular lot of latex. Similarly, although the degree of carboxylation is preferably within a certain range, the amount of antibody attached is determined independently of the precise degree of carboxylation of the core particles, i.e., by the less than stoichiometric amount of avidin bound to the carboxyl groups and then by the selected molar ratios of biotinic acid and biotinylated antibody. Thus reproducability of manufacture is significantly enhanced relative to prior latex particle-to-antibody linking procedures, particularly with respect to IgM, which previously had to be bound to the latex by the highly variable adsorption technique.

While the invention has been described in terms of certain preferred embodiments, modifications obvious to one with ordinary skill in the art may be made without departing from the scope of the present invention. For example, while it is not preferred, the amount of antibody bound to the particles could be made through control of the number of avidin molecules bound to the latex core particles followed by saturation of the biotin binding sites with biotinylated antibody molecules. While the diagnostic particle suspensions generally require that the antigen be large, having at least two antigenic determinant sites, it is also contemplated that a small antigenically active molecule or hapten could agglutinate the particles if the particles were suspended in a liquid medium that contained a chemical which would link two or more of the hapten molecules.

Various features of the present invention are set forth in the following claims:

What is claimed is:

1. A diagnostic particle comprising
a carboxylate-derivatized polymeric core between about 0.2 and about 1.0 micron in diameter,
a plurality of avidin moieties linked through amide bonds to said core,
a plurality of biotin moieties complexed to said avidin moieties, and
a plurality of antibody molecules linked through amide bonds to a significant portion of said biotin moieties, the amount of antibody molecules on the surface of said particle being controlled so that said diagnostic particle may be stably suspended in aqueous medium in the presence of like particles without agglutination, but subsequently agglutinate in the presence of a substance with which said antibody molecules react.

2. A diagnostic composition comprising a plurality of particles, each particle comprising a carboxylate-derivatized polymeric core between about 0.2 and about 1.0 micron in diameter, a plurality of avidin moieties linked through amide bonds to said core, a plurality of biotin moieties complexed to said avidin moieties and a plurality of antibody molecules linked through amide bonds to a significant portion of said biotin moieties and an aqueous medium in which said particles are suspended, the amount of antibody molecules on each of said particles being controlled so that said particles remain in suspension in said aqueous medium without agglutination, but when a substance reactive with said antibody molecules is introduced into said aqueous medium, said particles agglutinate.

3. A composition according to claim 2 wherein said particles cores are formed of a polymer selected from the group consisting of polyacrylamide and polystyrene.

4. A composition according to claim 2 wherein said particles have between about $10^{10}$ and about $10^{13}$ avidin molecules per cm$^2$ of surface area of said cores.

5. A composition according to claim 2 wherein said particles have between about $2 \times 10^{11}$ and about $2 \times 10^{12}$ antibody molecules per cm$^2$ of surface area of said cores.

6. A composition according to claim 2 wherein said diagnostic particles have neutralizing moieties attached to core surface carboxyl groups that are not linked by amide bonds to avidin.

7. A composition according to claim 2 wherein said diagnostic particles also include non-immunogenic proteinaceous material adsorbed on surfaces of said cores.

8. A composition according to claim 2 wherein said antibody molecules are monoclonal antibody molecules.

9. A composition according to claim 2 wherein said cores are carboxylated to between about 0.1 to about 0.5 milliequivalents per gram of core particles.

10. A method of preparing diagnostic particles comprising
providing carboxylate-derivatized polymeric core particles between about 0.2 and about 1.0 micron in diameter,
linking avidin molecules to said core particles through amide bonds,
binding biotin molecules to antibody molecules through amide bonds, and
complexing said core particle-linked avidin with a controlled amount of said antibody molecule-bound biotin, whereby said diagnostic particles may be suspended in aqueous medium without agglutination of said particles, but when a substance reactive with said antibody molecules is introduced into said aqueous medium, said particles agglutinate.

11. A method according to claim 10, providing core particles which are carboxylated to between about 0.1 and about 0.5 milliequivalents per gram of polymer.

12. A method according to claim 10 wherein said polymer is selected from the group consisting of polystyrene and polyacrylamide.

13. A method according to claim 12 wherein said polymer is polystyrene, and between about $1.2 \times 10^{-3}$ and about $1.2 \times 10^{-2}$ gm of avidin are linked per gram of core particles.

14. A method according to claim 12 wherein said polymer is polyacrylamide and between about $1.2 \times 10^{-3}$ and about $1.2 \times 10^{-2}$ gm of avidin are linked per gram of core particles.

15. A method according to claim 10 wherein said avidin is selected from the group consisting of egg white avidin and streptavidin.

16. A method according to claim 10 including neutralizing surface carboxyl groups of said core particles not bound to avidin.

17. A method according to claim 16 including adsorbing a non-immunogenic proteinaceous material onto the surface of said core particles subsequent to avidin linking and carboxyl group neutralization.

18. A method according to claim 10 controlling the amount of antibody molecules by complexing said core particle-linked avidin with a mixture of free biotinic acid and said antibody-bound biotin.

19. A method according to claim 18 controlling the amount of antibody molecules to provide between about $2 \times 10^{11}$ and about $2 \times 10^{12}$ antibody molecules per cm$^2$ of core particles surface area.

20. A method according to claim 19 wherein the molar ratio of said biotinic acid and said antibody-bound biotin is between about 1:1 and about 10:1.

21. A method according to claim 10 wherein said antibody is a monoclonal antibody.

22. A method according to claim 10 wherein linking said avidin to said core particles comprises reacting said core particles with a carbodiimide to form an intermediate and reacting said intermediate with avidin.

23. A method according to claim 22 wherein linking said biotin to said antibody comprises reacting said antibody with an N-hydroxy imide to form an ester intermediate and reacting said antibody with said ester intermediate.

24. A method according to claim 10, including suspending said diagnostic particles in a liquid medium to form a stable suspension.

25. A diagnostic particle in accordance with claim 1 wherein said particle has between about $2 \times 10^{11}$ and about $2 \times 10^{12}$ antibody molecules per cm$^2$ of surface area of said polymeric core.

26. A diagnostic particle in accordance with claim 1 wherein said antibody molecules are linked to a first significant portion of said biotin moieties and a second significant portion of said biotin moieties have no antibody molecules linked thereto.

27. A diagnostic particle comprising
a core between about 0.2 and about 1.0 micron in diameter formed of polymer selected from the group consisting of polyacrylamide and polystyrene, said polymer being carboxylated to between about 0.1 to about 0.5 milliequivalents per gram,
between about $10^{10}$ and about $10^{13}$ avidin molecules bound through amide bonds to said core per cm$^2$ of surface area,
neutralizing moieties attached to core surface carboxyl groups that are not linked by amide bonds to avidin,
additional non-immunogenic proteinaceous material adsorbed on surfaces of said cores,
biotin moieties complexed to said avidin moieties, and
about $2 \times 10^{11}$ and about $2 \times 10^{12}$ antibody molecules linked through amide bonds to biotin moieties per cm$^2$ of surface area of said core.

28. A suspension of diagnostic particles in accordance with claim 27 in an aqueous medium.

* * * * *